US011624740B2

(12) United States Patent
Pattison et al.

(10) Patent No.: US 11,624,740 B2
(45) Date of Patent: Apr. 11, 2023

(54) PROTECTIVE ENCLOSURE FOR GAS SENSORS

(71) Applicants: International Business Machines Corporation, Armonk, NY (US); The University of Melbourne, Melbourne (AU); Technische Universiteit Eindhoven, Eindhoven (NL)

(72) Inventors: Thomas Geoffrey Pattison, Melbourne (AU); Tom Van der Pol, Heeswijk-Dinther (NL); Linda Karin Sundberg, Los Gatos, CA (US); Krystelle Lionti, San Jose, CA (US); Andrea Fasoli, San Jose, CA (US); Luisa Dominica Bozano, Los Gatos, CA (US)

(73) Assignees: International Business Machines Corporation, Armonk, NY (US); The University of Melbourne, Melbourne (AU); Technische Universiteit Eindhoven, Eindhoven (NL)

( * ) Notice: Subject to any disclaimer, the term of this patent is extended or adjusted under 35 U.S.C. 154(b) by 229 days.

(21) Appl. No.: 16/932,584

(22) Filed: Jul. 17, 2020

(65) Prior Publication Data
US 2022/0018822 A1    Jan. 20, 2022

(51) Int. Cl.
*G01N 33/00* (2006.01)
*G01N 27/12* (2006.01)

(52) U.S. Cl.
CPC ....... *G01N 33/0014* (2013.01); *G01N 27/125* (2013.01); *G01N 27/127* (2013.01); *G01N 33/0024* (2013.01); *G01N 33/0031* (2013.01)

(58) Field of Classification Search
CPC ............. G01N 33/0014; G01N 27/125; G01N 27/127; G01N 33/0024; G01N 33/0031
See application file for complete search history.

(56) References Cited

U.S. PATENT DOCUMENTS 6,773,926 B1    8/2004   Freund et al.
8,336,402 B2    12/2012  Glezer et al.
(Continued)

FOREIGN PATENT DOCUMENTS

WO          03060500 A1       7/2003
WO    WO-2010025600 A1  *   3/2010    ......... G01N 33/0009

OTHER PUBLICATIONS

Agarwal et al., Graphitic carbon nanospheres: A Raman spectroscopic investigation of thermal conductivity and morphological evolution by pulsed laser irradiation, Journal of Applied Physics 118:214301.1-214301.6 (2015).
(Continued)

*Primary Examiner* — Benjamin R Schmitt
(74) *Attorney, Agent, or Firm* — Karen Canaan; CanaanLaw, P.C.

(57) ABSTRACT

A small-sized, portable enclosure protects a gas sensor against degradation due to environmental exposure and changes in atmospheric conditions. The protective enclosure includes an inlet for introduction of a gas into the enclosure, an outlet for release of the gas upon completion of a sensing run, and a number of in-line filters that remove from the inflowing gas sample analytes, contaminants, and other materials that can compromise the integrity of the sensor or cause the sensor to degrade over time. The enclosure does not include any filters during the measurement phase of the sensing run in order to allow the gas sensor to accurately measure an unmodified gas mixture and/or analyte.

21 Claims, 11 Drawing Sheets

(56) References Cited

U.S. PATENT DOCUMENTS

| | | | |
|---|---|---|---|
| 9,034,275 B2 | 5/2015 | Lee et al. | |
| 9,658,106 B2 | 5/2017 | Chou et al. | |
| 9,791,428 B2 | 10/2017 | Thomas et al. | |
| 2005/0142030 A1* | 6/2005 | Kim | G01N 27/127 422/400 |
| 2012/0036916 A1 | 2/2012 | Henshaw et al. | |
| 2015/0377868 A1* | 12/2015 | Cooper | G01N 1/22 436/128 |
| 2018/0024089 A1 | 1/2018 | Mickelson et al. | |
| 2018/0353885 A1 | 12/2018 | Swanson et al. | |
| 2020/0025399 A1* | 1/2020 | Dijkstra | G01N 15/06 |

OTHER PUBLICATIONS

Ansar et al., Quantitative Comparison of Raman Activities, SERS Activities, and SERS Enhancement Factors of Organothiols: Implication to Chemical Enhancement, The Journal of Physical Chemistry Letters 3:560-565 (2012).

Ansar et al., Organothiols Self-Assembled onto Gold: Evidence for Deprotonation of the Sulfur-Bound Hydrogen and Charge Transfer from Thiolate, The Journal of Physical Chemistry Letters C 117:8793-8798 (2013).

Ansar et al., Dispersion Stability, Ligand Structure and Conformation, and SERS Activities of 1-Alkanethiol Functionalized Gold and Silver Nanoparticles, The Journal of Physical Chemistry Letters C 118:24925-24934 (2014).

Brewer et al., Comparative Investigations of the Packing and Ambient Stability of Self-Assembled Monolayers of Alkanethiols on Gold and Silver by Friction Force Microscopy, The Journal of Physical Chemistry 108:4723-4728 (2004).

Chinwangso et al., Multidentate Adsorbates for Self-Assembled Monolayer Films, Accounts of Chemical Research 44(7):511-519 (2011).

Dascal et al., Chemiresistors Based on Bisdithiocarbamate Interlinked Gold Nanoparticles, Proceedings 2(933)1-4 (2018).

Dunn et al., Oxidation of sulfur dioxide to sulfur trioxide over supported vanadia catalysts, Applied Catalysis B: Environmental 19:103-117 (1998).

Fukushima et al., Microstructure, Wettability, and Thermal Stability of Semifluorinated Self-Assembled Monolayers (SAMs) on Gold, The Journal of Physical Chemistry B 104:7417-7423 (2000).

Garrell et al., Adsorption of Sulfur Containing Molecules on Gold: The Effect of Oxidation on Monolayer Formation and Stability Characterized by Experiments and Theory, The Journal of The American Chemical Society 117:11563-11571 (1995).

Gronbeck et al., Thiols and Disulfides on the Au(111) Surface: The Headgroup-Gold Interaction, The Journal of the Americal Chemical Society 112:3839-3842 (2000).

Hunt et al., Laser heating of sulfuric acid droplets held in air by laser Raman tweezers, RSC Advances 3:19448-19454 (2013).

Shida et al., Annealing Effect of Self-Assembled Monolayers Generated from Terphenyl Derivatized Thiols on Au (111), Langmuir 18:83-92 (2002).

Ishida et al., Stability of Terphenyl Self-Assembled Monolayers Exposed under UV Irradiation, Langmuir 18:10496-10499 (2002).

Konvalina et al., Sensors for Breath Testing: From Nanomaterials to Comprehensive Disease Detection, Accounts of Chemical Research 47(1):66-76 (2014).

Lee et al., Evaluation of Activated Carbon Filters for Removal of Ozone at the PPB Level, American Industrial Hygiene Association Journal 60:589-600 (1999).

Levin et al., Chain-Length-Dependent Vibrational Resonances in Alkanethiol Self-Assembled Monolayers Observed an Plasmonic Nanoparticle Substrates, Nano Letters 6(11):2617-2621 (2006).

Maciel et al., The stability of self-assembled monolayers with time and under biological conditions, Journal of Biomedical Materials Research A 94A(3):833-843(2010).

Peng et al., Diagnosing lung cancer in exhaled breath using gold nanoparticles, Nature Nanotechnology 4:669-673 (2009).

Peris et al., On-line monitoring of food fermentation processes using electronic noses and electronic tongues: A review, Analytica Chimica Acta 804:29-36 (2013).

Rambukwella et al., Ligand Structure Determines Nanoparticles' Atomic Structure, Metal-Ligand Interface and Properties, Frontiers in Chemistry 6(330):1-17 (2018).

Saisaha et al., Mechanism of Alkene, Alkane, and Alcohol Oxidation with H2O2 by an in Situ Prepared Mnll/Pyridine-2-carboxylic Acid Catalyst, ACS Catalysis 6:3486-3495 (2016).

San et al., Synthesis of Alkanethiolate-Capped Metal Nanoparticles Using Alkyl Thiosulfate Ligand Precursors: A Method to Generate Promising Reagents for Selective Catalysis, Nanomaterials 8(346):1-21 (2018).

Schoenfisch et al., Air Stability of Alkanethiol Self-Assembled Monolayers on Silver and Gold Surfaces, Journal of the American Chemical Society 120(18):4502-4513 (1998).

Sekhar et al., Chemical Sensors for Environmental Monitoring and Homeland Security, The Electrochemical Society Interface 19:35-40 (2010).

Shlomi et al., Detection of Lung Cancer and EGFR Mutation by Electronic Nose System, Journal of Thoracic Oncology 12(10):1544-1551 (2017).

Silva-De Hoyos et al., Plasmonic and fluorescent sensors of metal ions in water based on biogenic gold nanoparticles, Arabian Journal of Chemistry 13:1975-1985 (2020).

Singhana et al., Self-Assembled Monolayer Films Derived from Tridentate Cyclohexyl Adsorbates with Alkyl Tailgroups of Increasing Chain Length, Langmuir 29:14108-14116 (2013).

Srisombat et al., Stability: A key issue for self-assembled monolayers on gold as thin-film coatings and nanoparticle protectants, Colloids and Surfaces A: Physiochemical and Engineering Aspects 390:1-19 (2011).

Tomikawa et al., Raman Study of Sulfuric Acid at Low Temperatures, Journal of Physical Chemistry 102 (30):6082-6088 (1998).

Vericat et al., Self-assembled monolayers of thiols and dithiols on gold: new challenges for a well-known system, Chemical Society Reviews 39:1805-1834 (2010).

Willey et al., Rapid Degradation of Alkanethiol-Based Self-Assembled Monolayers on Gold in Ambient Laboratory Conditions, Lawrence Livermore National Laboratory, Surface Science, UCRL-JRNL-205694, Elsevier Science (2004).

* cited by examiner

PROTECTIVE ENCLOSURE FOR GAS SENSORS

TECHNICAL FIELD

The present invention relates generally to gas sensors and more specifically to a protective enclosure for gas sensors.

BACKGROUND OF THE INVENTION

Electronic nose devices are attracting increasing attention as the Internet of Things (IoT) is taking shape. Electronic nose devices generally include a multi-gas sensor array whereupon exposure to a gaseous odor, the collective output of the sensors associates a unique fingerprint to the odor, which is used to discriminate the individual volatiles of the gaseous odor. The individual volatiles are used to label the detected odor and/or identify process anomalies and/or deviations from given standards. Gas sensors are important for IoT devices since they provide the data that are used by cloud computing to generate meaningful output through Machine Learning and artificial intelligence (AI).

Electronic nose devices currently in use suffer from gas sensor degradation. Aging and changes in atmospheric conditions lead gas sensors to undergo changes in sensing material morphology, composition, electrical behavior over time, and surface poisoning from external contamination, etc. Sensor degradation ultimately leads to a decrease in performance, compromising the proper functioning and reliability of an electronic nose device. Attempts to alleviate gas sensor degradation through techniques, such as storing sensors under vacuum and only injecting gaseous analytes when gas sensing measurements are taken have proven to be ineffective for several reasons, including the requirement for bulky expensive equipment and limitations on the timing at which the measurements may be taken. The use of filters to remove deleterious and unwanted gases during the sensing measurements has also been ineffective, because filters are never completely specific and can filter out a broad range of gases, including analytes of interest.

There remains a need in the art for a gas sensing device that is specific, efficient, and portable.

SUMMARY OF THE INVENTION

The present invention overcomes the need in the art by providing a protective enclosure for gas sensors.

In one aspect, the present invention relates to a method, comprising: (i) providing an enclosure comprising an inlet, at least one outlet, at least one filter, and a sensor that detects an analyte of interest; (ii) introducing a gas comprising the analyte of interest through the inlet, wherein the sensor detects the analyte of interest in the gas, the gas exits the enclosure through the at least one outlet after detection, the gas does not contact the at least one filter between input of the gas through the inlet and exit of the gas through the at least one outlet, and the gas further includes at least one deleterious compound that degrades performance of the sensor; (iii) introducing an additional influx of the gas through the inlet, wherein the additional influx of the gas passes through the at least one filter prior to contacting the sensor, wherein the at least one filter removes the at least one deleterious compound from the additional influx of the gas; and (iv) allowing the additional influx of the gas that is free of the deleterious compounds to remain in contact with the sensor.

In another aspect, the enclosure further comprises at least two valves, one of which opens and closes the inlet and another of which opens and closes at least one outlet.

In another aspect, the inlet and one of the at least one outlet are open at step (ii) and both the inlet and the at least one outlet are closed at step (iv).

In a further aspect, the at least one filter is a retractable filter situated at the inlet, wherein the at least one retractable filter retracts at step (ii) so that the gas may enter the enclosure as an unfiltered gas, and is repositioned at the inlet in step (iii) so that the additional influx of gas must pass through the at least one retractable filter to contact the gas sensor.

In another aspect, steps (ii) and (iii) operate in a timeframe ranging from one second to no longer than 12 hours.

In another aspect, the enclosure further comprises a sensing gas line, a purge gas line, and a valve at the inlet to direct the gas from the inlet into the sensing gas line and/or the purge gas line, wherein the sensing gas line has no filters and the at least one filter is situated in the purging gas line.

In one embodiment, the present invention relates to a device comprising: an enclosure; an inlet for input of a gas; a sensing gas line with no filters; a purge gas line with at least one filter to remove deleterious compounds from the gas; an inlet valve to open and close the inlet and direct flow of the gas into the sensing gas line and/or the purge gas line; a gas sensor with access to the sensing gas line and the purge gas line, wherein the gas sensor has (i) a first valve to cut off access of the gas sensor to the sensing gas line and (ii) a second valve to cut off access of the gas sensor to the purge gas line; at least one outlet to exhaust the gas from the sensing gas line and the purge gas line; and at least one outlet valve to direct the exhaust from the sensing gas line and purge gas line out of the enclosure, wherein the at least one outlet valve is a one-way valve that prevents outside air from entering the enclosure.

In a further embodiment, the gas is an analyte of interest that enters the enclosure through the inlet, the inlet valve directs the analyte of interest into the sensing gas line for measurement by the gas sensor, and after measurement, the analyte of interest leaves the enclosure through one of the at least one outlet.

In another embodiment, the gas is a flushing gas that enters the enclosure through the inlet, the inlet valve directs the flushing gas into the purge gas line, wherein the flushing gas passes through the at least one filter, over the gas sensor, and exits the enclosure through one of the at least one outlet.

In a further embodiment, the inlet valve closes the inlet, and the at least one outlet valve closes the at least one outlet, thereby sealing the enclosure so that the flushing gas circulates within the sealed enclosure.

In another embodiment, the present invention relates to a device comprising: an enclosure; an inlet for input of a gas; an inlet valve for closing the inlet; at least one retractable filter for removing deleterious compounds from the gas, wherein the at least one retractable filter is situated at the inlet; an outlet for exit of the gas; an outlet valve for closing the outlet; and a gas sensor with access to the inlet and the outlet, wherein the gas sensor is (i) sealed from the inlet via closure of the inlet valve and (ii) sealed from the outlet via closure of the outlet valve.

In a further embodiment, the gas is an analyte of interest that enters the enclosure through the inlet where the at least one filter removes deleterious compounds from the gas, wherein the filtered gas passes onto the gas sensor for measurement and after measurement, the analyte of interest leaves the enclosure through the outlet.

In another embodiment, the gas is a flushing gas that enters the enclosure through the inlet, passes over the gas sensor, and remains within the enclosure until released by the outlet, wherein upon entry of the flushing gas into the gas sensor, the inlet valve and the outlet valve close and seal the enclosure, thereby preventing escape of the flushing gas.

In other aspects and embodiments, the sensor is selected from the group consisting of a metal oxide thin film, a metal oxide nanostructure, and a metal nanoparticle.

In further aspects and embodiments, the sensor is a metal nanoparticle sensor, wherein the metal is selected from the group consisting of gold, silver, platinum, and palladium.

In other aspects and embodiments, the gas sensor is a metal nanoparticle ligated with a thiol.

In further aspects and embodiments, the metal nanoparticle sensor is ligated with a thiol selected from the group consisting of ethanethiol, hexanethiol, octanethiol, decanethiol, dodecanethiol, and combinations thereof.

In other aspects and embodiments, the at least one filter is selected from the group consisting of activated carbon, silica gel, and combinations thereof.

In further aspects and embodiments, the at least one filter is a replaceable filter.

In other aspects and embodiments, the at least one deleterious compound is selected from the group consisting of ozone, silicone, chlorine, particulates, sediment, volatile organic compounds, and combinations thereof.

Additional aspects and embodiments of the invention will be provided, without limitation, in the detailed description of the invention that is set forth below.

BRIEF DESCRIPTION OF THE DRAWINGS

FIGS. 2A-2C are schematics showing different states of the sensor enclosure of FIG. 1.

FIGS. 9A and 9B show the effects of ozone contamination on decanethiol-ligated Au-NPs.

DETAILED DESCRIPTION OF THE INVENTION

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," comprises," and "comprising," as used in the specification and appended claims, specify the presence of the expressly recited components, elements, features, and/or steps, but do not preclude the presence or addition of one or more other components, elements, features, and/or steps.

As used herein, the terms "gas sensor" and "sensor" are used to refer to a single gas sensor or to a gas sensor array. Plural versions of the terms are used to refer to more than one gas sensor or gas sensor array. Unless expressly stated herein, reference to a single gas sensor in the following description will also include more than one gas sensor or sensor array.

The present invention provides a small-sized, portable enclosure that protects a gas sensor against degradation due to environmental exposure and changes in atmospheric conditions. The protective enclosure includes an inlet for introduction of a gas into the enclosure, an outlet for release of the gas upon completion of a sensing run, and a number of in-line filters. The purpose of the filters is to remove from the inflowing gas sample any analytes, contaminants, and other materials that can compromise the integrity of the sensor or cause the sensor to degrade over time. The enclosure does not include any filters during the measurement phase of the sensing run in order to allow the gas sensor to accurately measure an unmodified gas mixture and/or analyte. The filters that remove deleterious gaseous species that lead to degradation of gas sensors are only activated during the flushing and idle periods of the gas sensing process. The filter thus serves to flush the sensor array with gas in order to protect it. The type of filters used within the enclosure may differ based upon various factors, including: the gases introduced into the enclosure, the gases intended to be removed, and/or the materials used in the sensor array. In one embodiment, the filters are replaceable once expended. Once the deleterious gases have been removed from the gas influx flow, the inflowing gas sample may be used to flush the sensing array of materials of compounds that may otherwise degrade the sensor during idle periods. By preventing sensor degradation during the idle periods of the gas sensing process, the lifetime of the gas sensor can be increased, thus leading to a wider range of applications for any particular gas sensor.

Examples of gas sensors that may be used with the protective enclosures described herein, include, without limitation, gas chromatography mass spectrometers (GCMSs), Fourier-transform infrared spectrometers (FTIRs), electrochemical (EC) sensors, quartz crystal microbalances (QCMs), metal oxide thin films, metal oxide nanostructures, and metal nanoparticle sensors, and combinations thereof. Examples of metal oxides that may be used for metal oxide thin films or nanostructures include, without limitation, aluminum oxide ($Al_2O_3$), ceric dioxide ($CeO_2$), cuprous oxide ($Cu_2O$), cupric oxide (CuO), copper peroxide ($CuO_2$), copper(III) oxide ($Cu_2O_3$), indium oxide ($In_2O_3$), ferric oxide ($Fe_2O_3$), iron(II) oxide FeO, iron(II,III) oxide ($Fe_3O_4$), manganese dioxide ($MnO_2$), tin(IV) oxide ($SnO_2$), titanium dioxide ($TiO_2$), tungsten trioxide ($WO_3$), zinc oxide (ZnO), and combinations thereof. Examples of metal nanoparticle sensors include, without limitation, gold (Au), silver (Ag), platinum (Pt), and palladium (Pd) nanoparticle sensors. Metal nanoparticles will typically be ligated with a thiol (R—SH) for protective purposes. Examples of thiols that may be ligated to metal nanoparticles includes, without limitation, organothiols, such as ethanethiol, hexanethiol, octanethiol, decanethiol, dodecanethiol, and combinations thereof.

Examples of filtering materials or devices that may be used in the gas sensor enclosures described herein include, without limitation, activated carbon filters, silica gel, catalytic converters, and combinations thereof. Activated carbon filters may remove some or all of the following deleterious compounds from a gas sample: ozone, silicone, chlorine, particulates, sediment, volatile organic compounds (VOCs), and combinations thereof. Silica gel filters may be used to remove moisture. Catalytic converters may be used to decompose ozone into oxygen by catalyzing a metal selected from the group consisting of iridium (Ir), osmium (Os), palladium (Pd), platinum (Pt), rhodium (Rh), ruthenium (Ru), and combinations thereof.

In order to control the flow of gas into, out of, and through the enclosure, the enclosure is equipped with one-way and two-way valves, as appropriate. Gas input flow may be driven from the environment by a small pump or directly by an external source (e.g., a person exhaling into the device). Valves may be operated using a program, such as for example, LABVIEW® (National Instruments Corp., Austin, Tex.). One type of valve that may be used in the enclosure at the inlet is a Y-valve that may be adjusted to allow the gas flow to be directed towards the gas sensor for measurement (where the enclosure is free of filters) and later adjusted so that the gas flow may circulate through the enclosure and encounter the filters that will clear the gas flow of deleterious compounds that might otherwise degrade the sensors.

Figure 1:
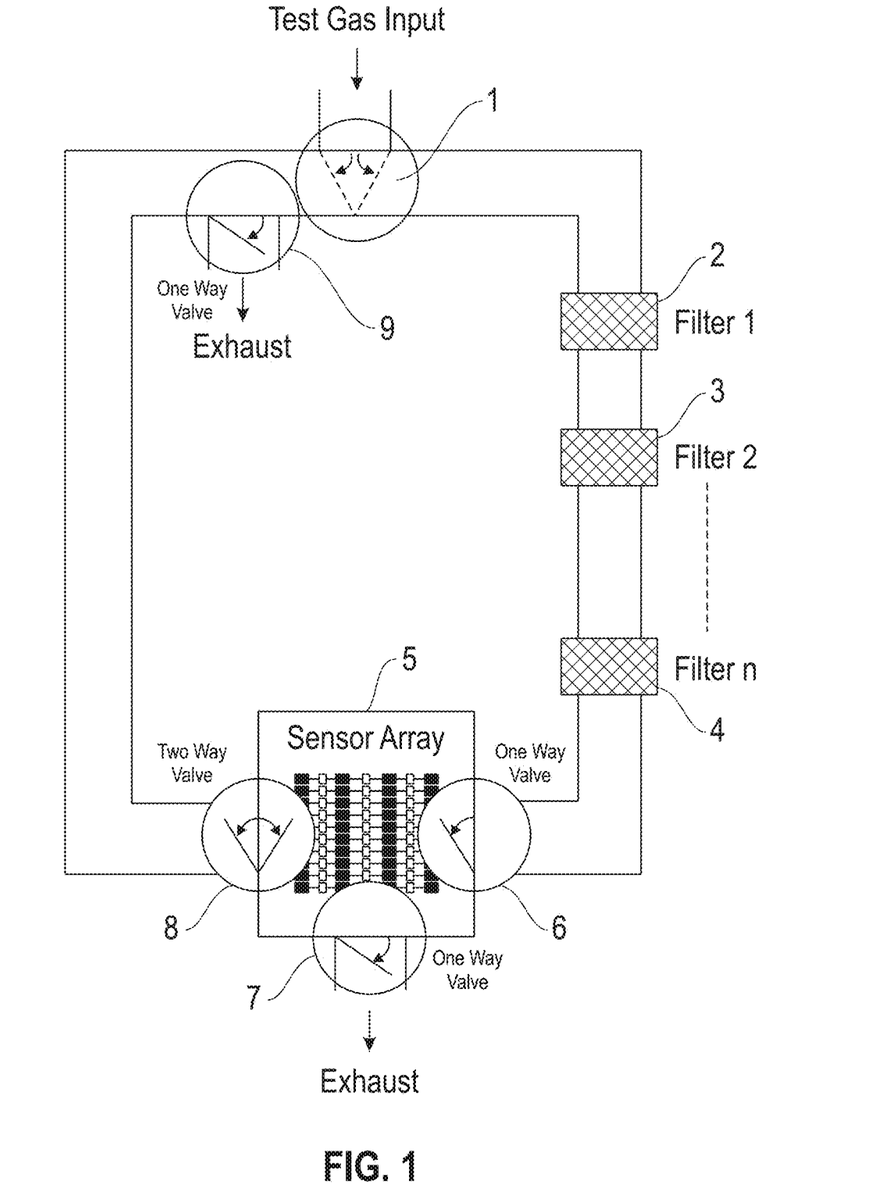
FIG. 1 is a schematic of an embodiment of the sensor enclosure described herein.

With reference to FIG. 1, in one embodiment, the gas sensor enclosure may include a valve to control direction of gas flow during sensing/purging/idle modes 1 and at least one in-line contaminant filter. Examples of in-line contaminant filters include, without limitation, an in-line contaminant filter 2 to remove moisture (e.g., silica gel) and an in-line contaminant filter 3 to remove/convert ozone (e.g., activated carbon). Additional in-line contaminant filters 4 may be added to the enclosure. The in-line contaminant filters 2, 3, and 4 can be removed and replaced as the filters become spent. The enclosure may also include a sensor housing 5 and several one-way and two-way valves, such as for example, a one-way valve to prevent flow during sensing and to allow flow during purging 6; a one-way exhaust valve to prevent contamination of sensors by unfiltered outside atmosphere, exhaust sensing gas flow, and direct purge gas flow 7; a two-way valve to allow forward flow of the sensing and purging gas and which seals to protect the sensors 8; and a one-way valve to purge exhaust gas flow 9. The two-way valve 8 will seal in order to protect the sensors and the one-way valve 9 will be closed during the sensing mode.

Figure 2A:
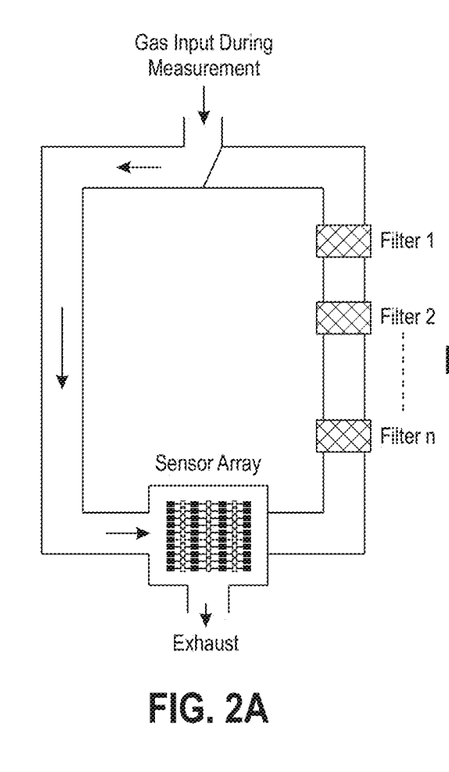
FIG. 2A shows a measurement phase.
Figure 2B:
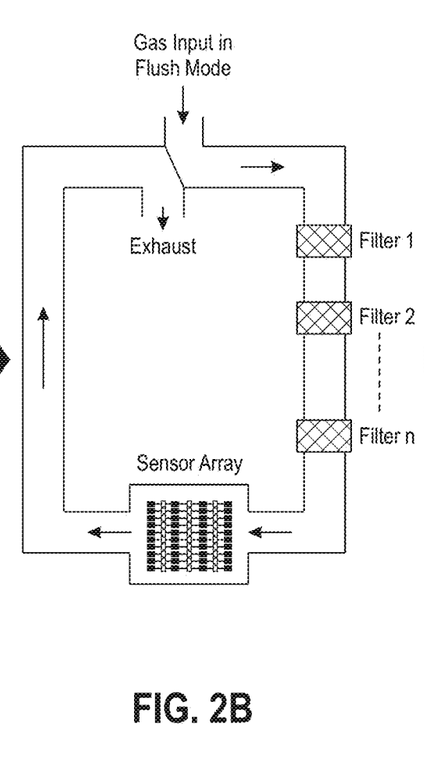
FIG. 2B shows a flush mode.
Figure 2C:
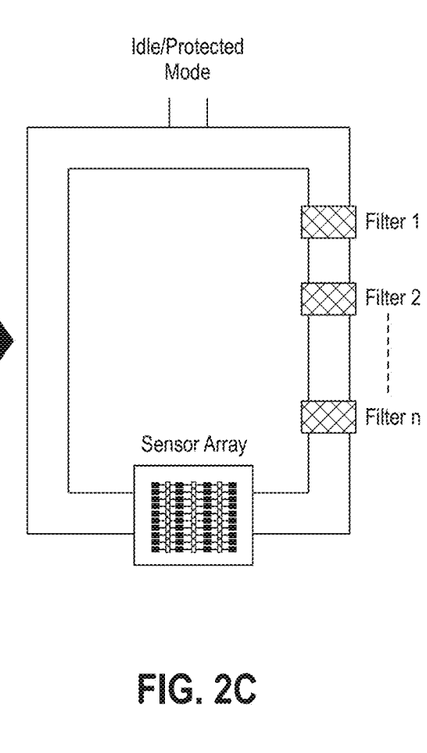
FIG. 2C shows an idle phase of the sensor enclosure.

FIGS. 2A-C illustrates three different modes of application of the exemplary gas sensor enclosure of FIG. 1. The different modes mitigate degradation of the gas sensors and/or gas sensor arrays housed within the enclosure.

FIG. 2A shows application of the gas sensor enclosure for gas measurement. In this embodiment, an unmodified gas is input directly into the sensor enclosure towards a sensor array through a one-way inlet. Once within the enclosure, the gas is measured in the sensor array and upon completion of the gas sensing, the sample exits the enclosure through a one-way exhaust outlet.

FIG. 2B shows application of the gas sensor enclosure for gas measurement followed by a flush mode. In this embodiment, an unmodified gas is input directly into the in-line filters to remove deleterious gas species and any remaining static and/or unfiltered gas analyte in the enclosure. Once sensing has completed and the measurement mode is finished, the gas sample may be continually fed into the enclosure as part of a "flush mode" where no sensing is taking place. The flush mode is designed to purge the enclosure of any contaminants or analyte remaining on the sensor array or in the enclosure that may accelerate sensor degradation, especially during idle periods, which occur between sensing periods. During the flush mode, the enclosure routes the incoming sample (containing carrier gases, analytes, contaminants, etc.) through a series of filters in the enclosure to remove contaminants and other species that may degrade the sensors within the array. The removal of species present in the gas sample results in the flushing of the enclosure, including the gas sensor chamber, with contaminant-free carrier gas resulting in the protection of the sensor array from contaminants, thus mitigating any degradation and loss of sensitivity to the sensor array within the enclosure. The filters, as part of the enclosure, may be removed and replaced with new filters after a set period of time or once consumed or saturated. This embodiment allows for the ongoing use of the sensing components and the enclosure, thus prolonging the use of a gas sensor in an environment where it would normally degrade in a relatively short period of time.

FIG. 2C shows another application of the gas sensor enclosure for gas measurement followed by an "idle mode." In this embodiment, the gas is input into the device for measurement as provided in FIG. 2A, followed by the flush mode of FIG. 2B. During the idle mode, the input and output valves of the device are closed, effectively sealing off the sensor array from inflowing mixtures that may compromise the sensor array. Because the closing off of the enclosure occurs immediately after the flush mode, the gases that have passed through the filters blanket the sensor, resulting in a significantly reduced chance of exposure of the sensor to materials that could degrade the sensitivity of the sensor or reduce its lifetime. Gas remaining in the idle mode is released from the enclosure by opening an exit valve that does not compromise the sensor array (e.g., the exhaust near the input in FIGS. 2B and 2C).

Figure 3:
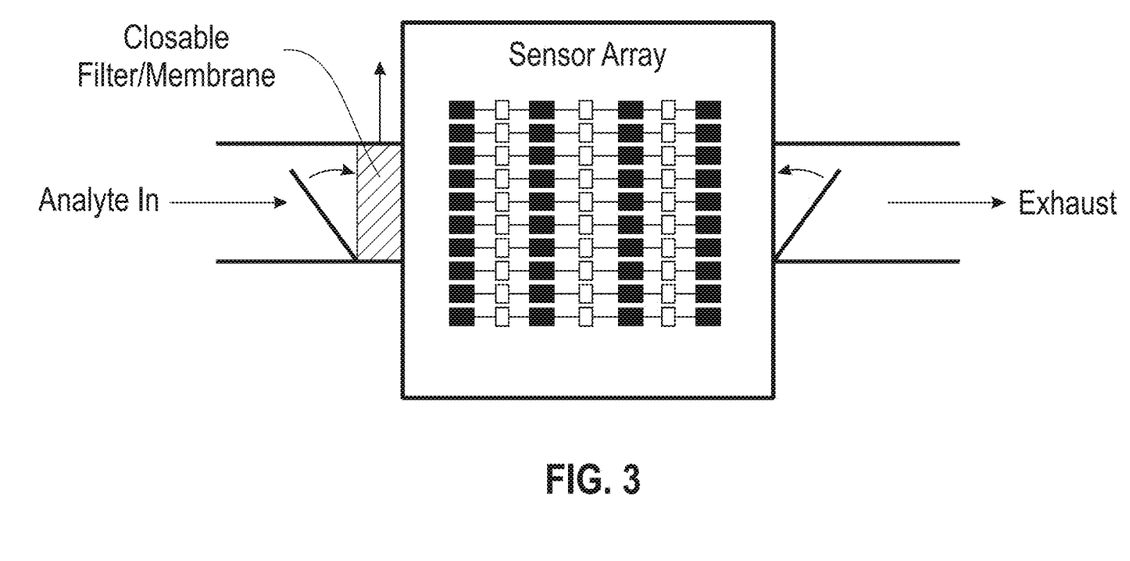
FIG. 3 is a schematic of another embodiment of the sensor enclosure.

With reference to FIG. 3, in a further embodiment, a gas sensor housed within an enclosure has one input line with one or more filters that can move as appropriate for the measurement, flushing, and idle modes of the gas sensor enclosure. In this embodiment, a sensor array is housed within an enclosure comprising a single input and a single output (exhaust) and only a single path for the gas to travel through. Similar to the embodiments of FIGS. 2A-2C, the measurement mode results in unencumbered flow of the gas through the sensor array and the subsequent exhaust of the sensed gas through the outlet. During the flush mode and idle modes, a retractable filter, which is retracted during the measurement mode, is placed in line with the input so that the path of incoming gas must flow through the filter before coming in contact with the sensor array. Once sufficient flow through the enclosure has been reached, or sufficient time has passed, the enclosure enters the idle mode where the input and the exhaust are closed off, sealing the sensor array.

The design of the enclosure allows for the measurement and flushing modes to occur quickly within a time period of one minute to no more than 12 hours. The idle mode may remain in place until such time that a new gas is introduced into the enclosure for measurement by the gas sensor.

One type of gas sensor in frequent use is a metal nanoparticle sensor. The sensing ability of metal nanoparticle sensors is dictated by the inter-particle distance, which is itself influenced by the choice of functionalizing ligand. One ligand/metal nanoparticle combination that is frequently used is organothiol ligands with gold nanoparticles, the latter of which have the characteristics of strong S—Au bonds and chemical resistance. Like other chemiresistors currently in use, self-assembled monolayers of organothiols on flat gold surfaces degrade in ambient conditions. Such degradation has also been observed on organothiols covalently attached to gold nanoparticles, the latter of which is used in Examples 1 and 2 to demonstrate that the protective enclosures described herein are capable of mitigating such degradation.

Figure 6A:
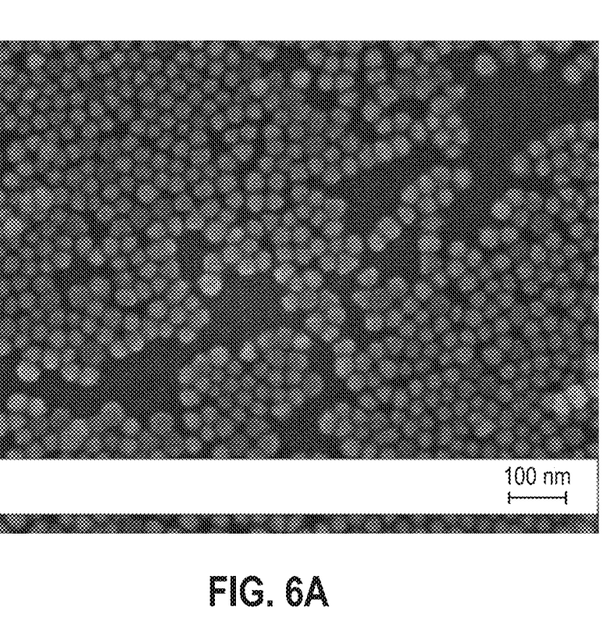
FIGS. 6A and 6B are SEM (scanning electron microscopy) micrographs of a hexanethiol-ligated Au-NP immediately after deposition (FIG. 6A) after aging in open ambient air for 13 days (FIG. 6B).
Figure 6B:
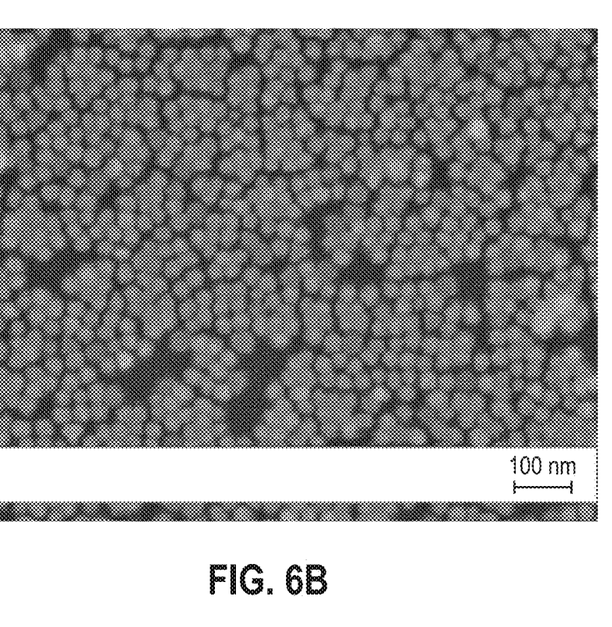
Figure 7:
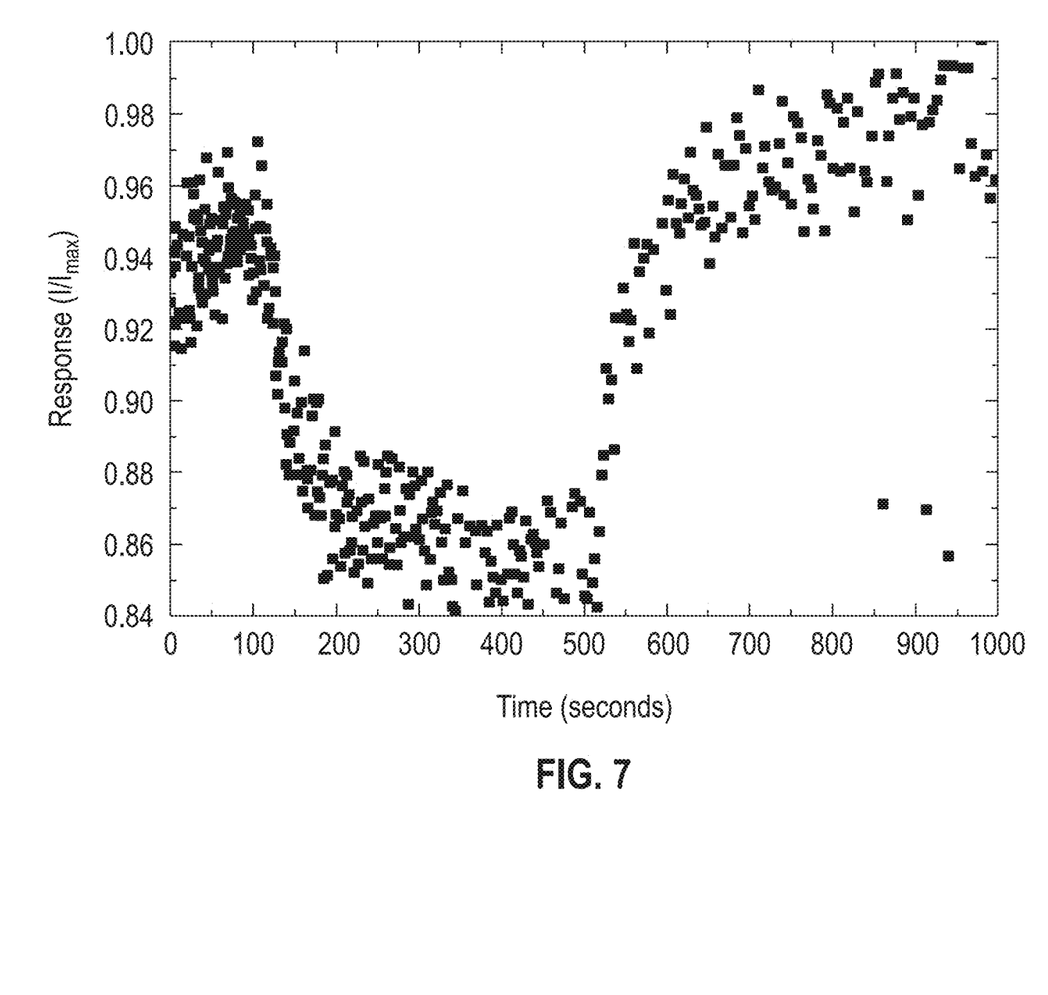
FIG. 7 is a graph showing the relative change in current (Response) over time of a sensor comprised of decanethiol-ligated Au-NPs aged for 14 days in a sealed container and exposed between t=100 sec to t=500 sec to 12678 ppm of octane in an $N_2$ stream.
Figure 8:
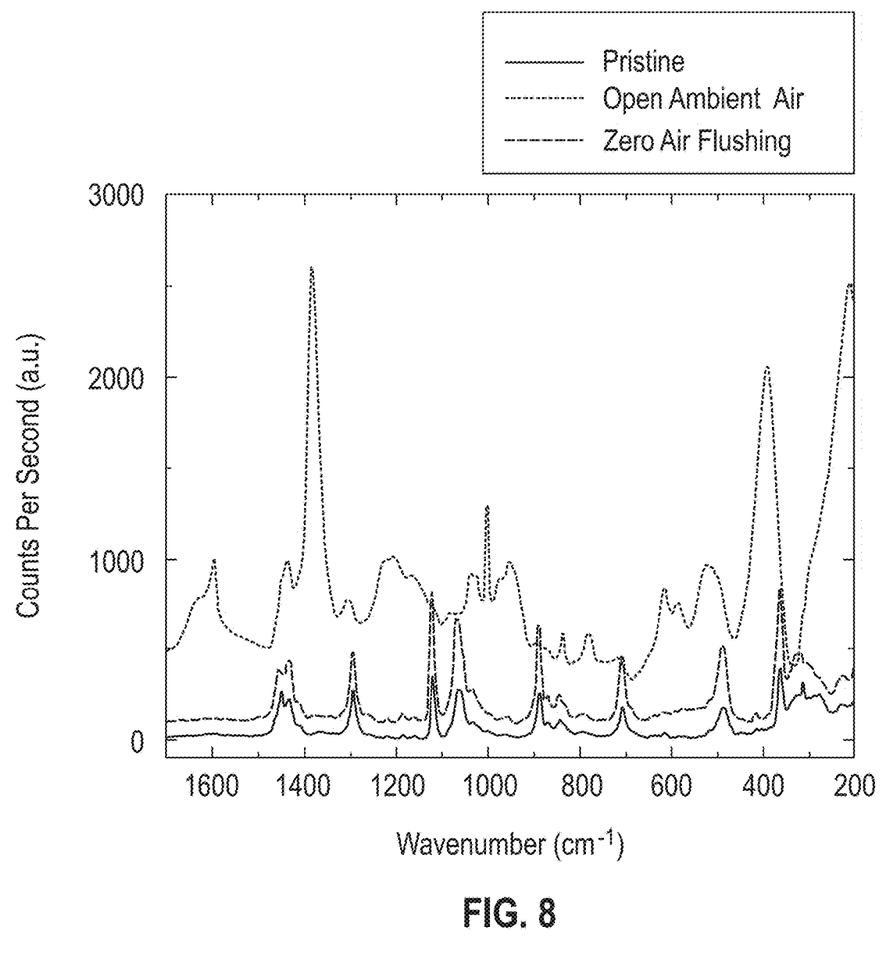
FIG. 8 is a graph showing SERS spectra results for decanethiol-ligated Au-NPs under the following conditions: pristine; after 24 hours of storage in freely exchanging ambient air; and after 24 hours of flushing with zero-air (synthetic mixture of 80% and 20% oxygen).
Figure 9A:
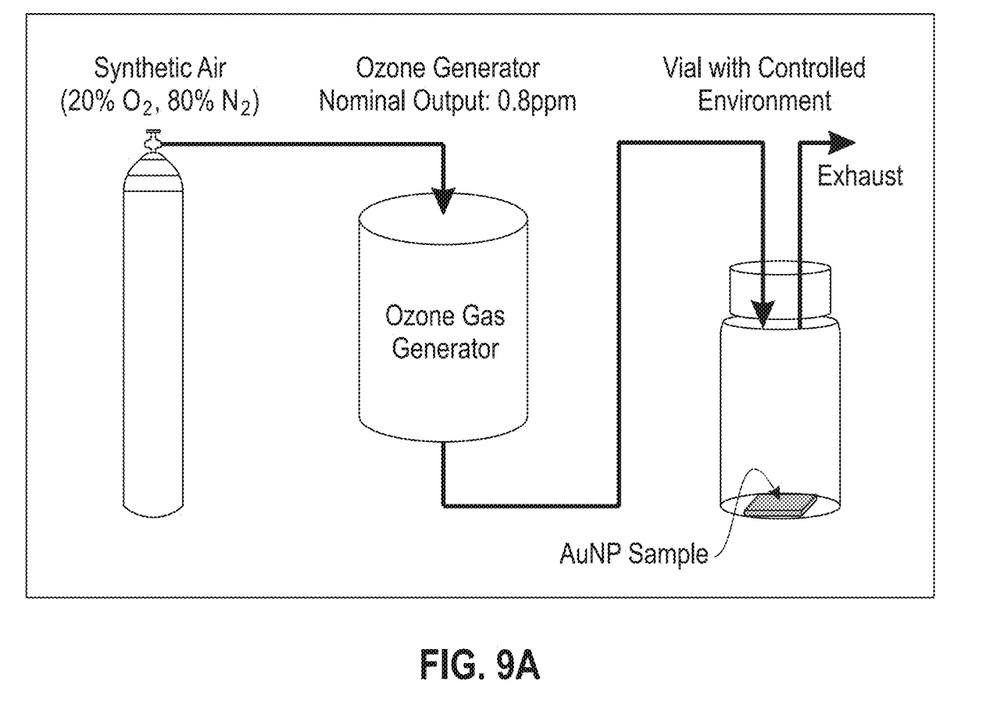
FIG. 9A is a schematic depicting a set-up for the introduction of ozone contaminant into zero-air atmosphere and the subsequent flow over to a sensor.
Figure 9B:
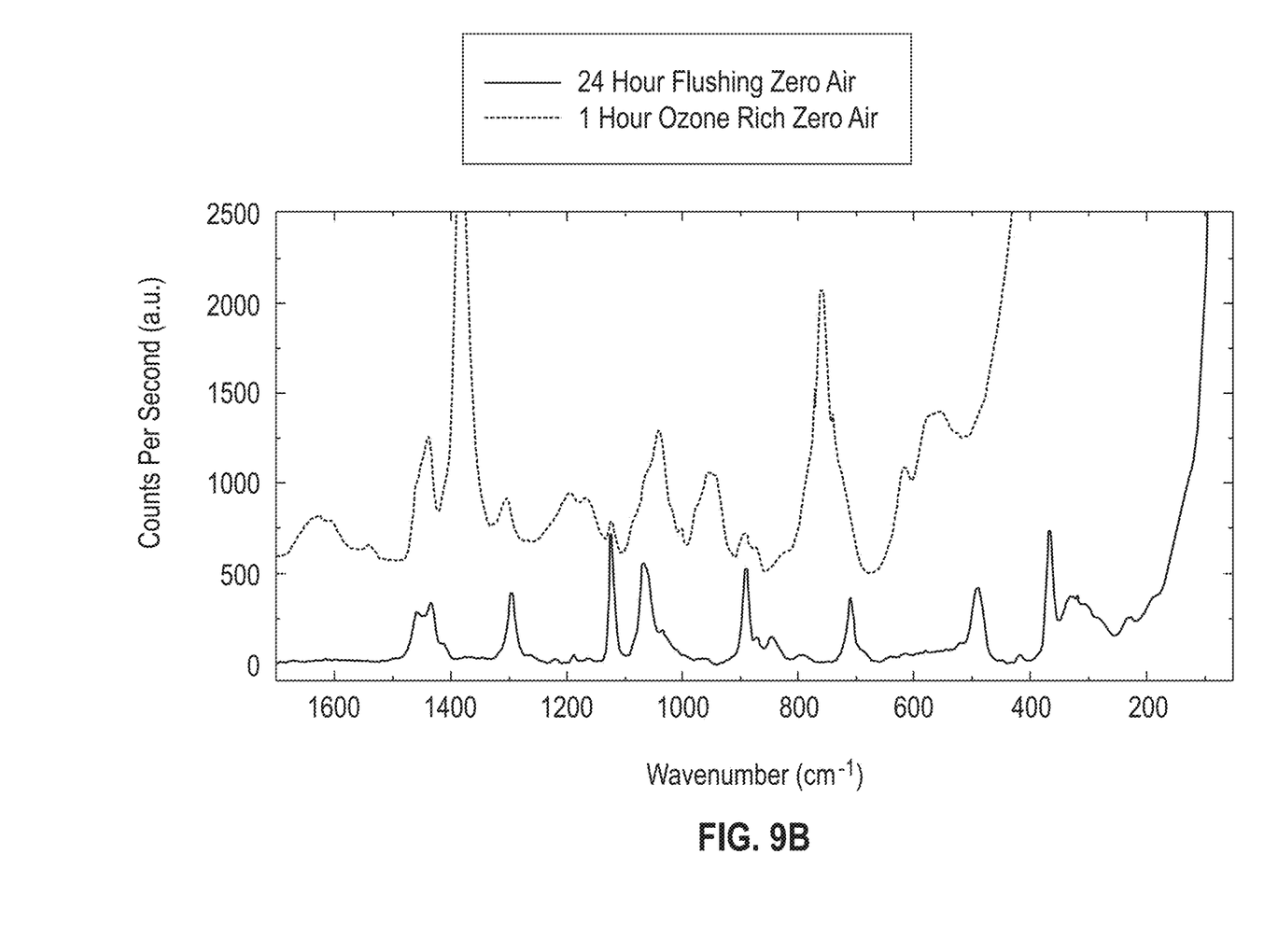
FIG. 9B is a graph showing SERS spectra results of decanethiol-ligated Au-NPs under the following conditions: 24 hours of flushing with zero-air; and 24 hours of flushing with zero-air followed by one hour where zero-air was enriched with ozone.

FIGS. 4-9 show the results of the experiments conducted in Examples 1 and 2 on gold nanoparticles (Au-NPs) ligated to decanethiol or hexanethiol. FIGS. 4-7 are directed to Example 1, which tested the effect that confinement has on the degradation of ligands surrounding Au-NPs; and FIGS. 8 and 9 are directed to Example 2, which tested the effect of removing deleterious gases on a sensor enclosure. It is to be understood that the chemiresistive ligated gold nanoparticles were used solely as an example of a chemiresistor and are not meant to be limiting with respect to any particular chemiresistor, gas sensor, and/or gas sensor array that may be used with the enclosure described herein. The gas sensor enclosure is designed to be used with any type of sensing technology where environmental exposure may decrease either the working lifetime of a sensor and/or the sensitivity of the sensing technology.

Figure 4A:
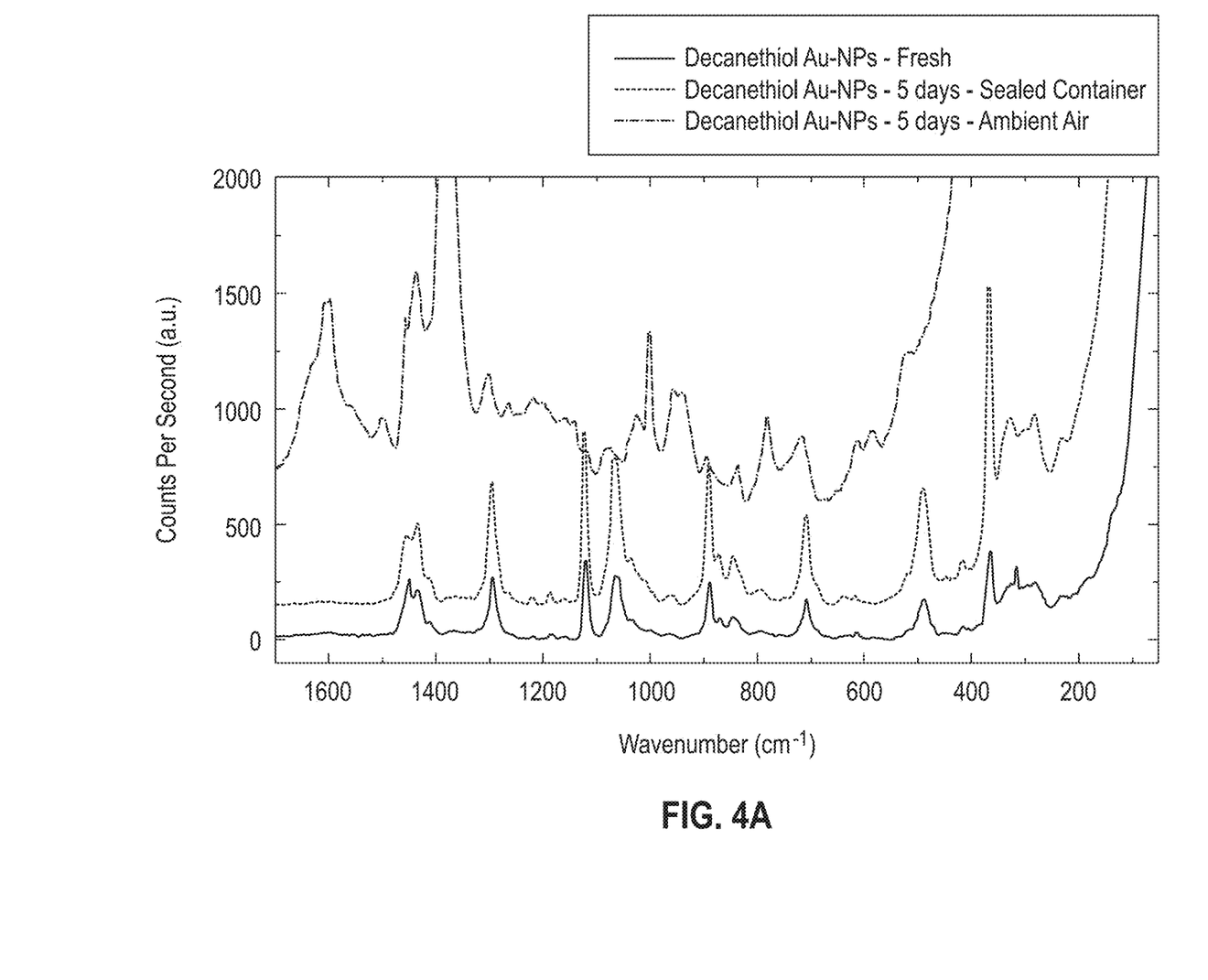
FIGS. 4A and 4B are graphs showing SERS (surface enhanced Raman spectroscopy) spectra results for decanethiol-ligated gold nanoparticles (Au-NPs) (FIG. 4A) and hexanethiol-ligated Au-NPs (FIG. 4B) under the following conditions: pristine (i.e., a fresh sample directly after deposition), ambient air (exposure to open-air), and sealed (within a 25 mL contained volume).
Figure 4B:
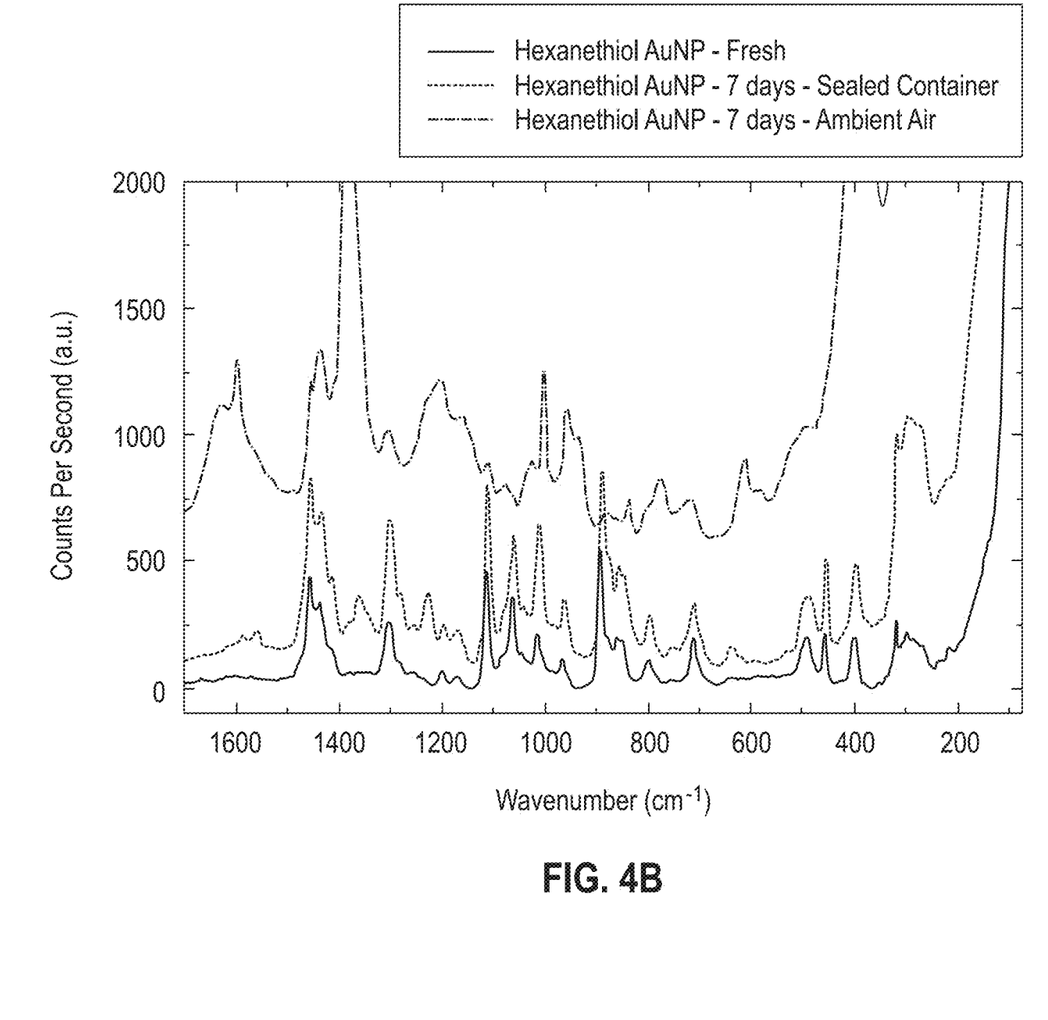

FIG. 4A shows SERS (surface enhanced Raman spectroscopy) spectra of decanethiol-ligated Au-NPs directly after deposition, after 5 days of storage in a confined 25 mL volume of ambient air, and after 5 days of storage in freely exchanging ambient air. FIG. 4B shows SERS spectra of hexanethiol-ligated Au-NPs directly after deposition, after 7 days of storage in a confined 25 mL volume of ambient air, and after 7 days of storage in freely exchanging ambient air. The decanethiol and hexanethiol ligands were covalently attached to the Au-NPs and provided colloidal stability of the Au-NPs. As can be seen for both types of ligands (referred to collectively as "thiol ligands"), the Au-NPs stored in the confined volume (also referred to herein as "enclosed" or "sealed" conditions) showed a very similar SERS spectra to that of freshly deposited ligated gold nanoparticles (also referred to herein as "pristine" conditions), suggesting no significant ligand degradation took place. By contrast, the particles stored in freely exchanging ambient air (also referred to herein as "open-air" or "open ambient air" conditions) showed a completely different spectrum that is attributed to the degraded thiol ligands. With reference to FIG. 4A, the peaks between 1298-1123 $cm^{-1}$ and 1062-873 $cm^{-1}$ are generally ascribed to SOS-species, and the broad set of peaks ranging from 1750 $cm^{-1}$ to 1500 $cm^{-1}$, the strong peak at 1378 $cm^{-1}$, and the sharp peak at 1000 $cm^{-1}$ are known fingerprints for graphitic carbon, indicating that the decanethiol ligand has degraded into SOS-species and graphitic carbon.

Figure 5:
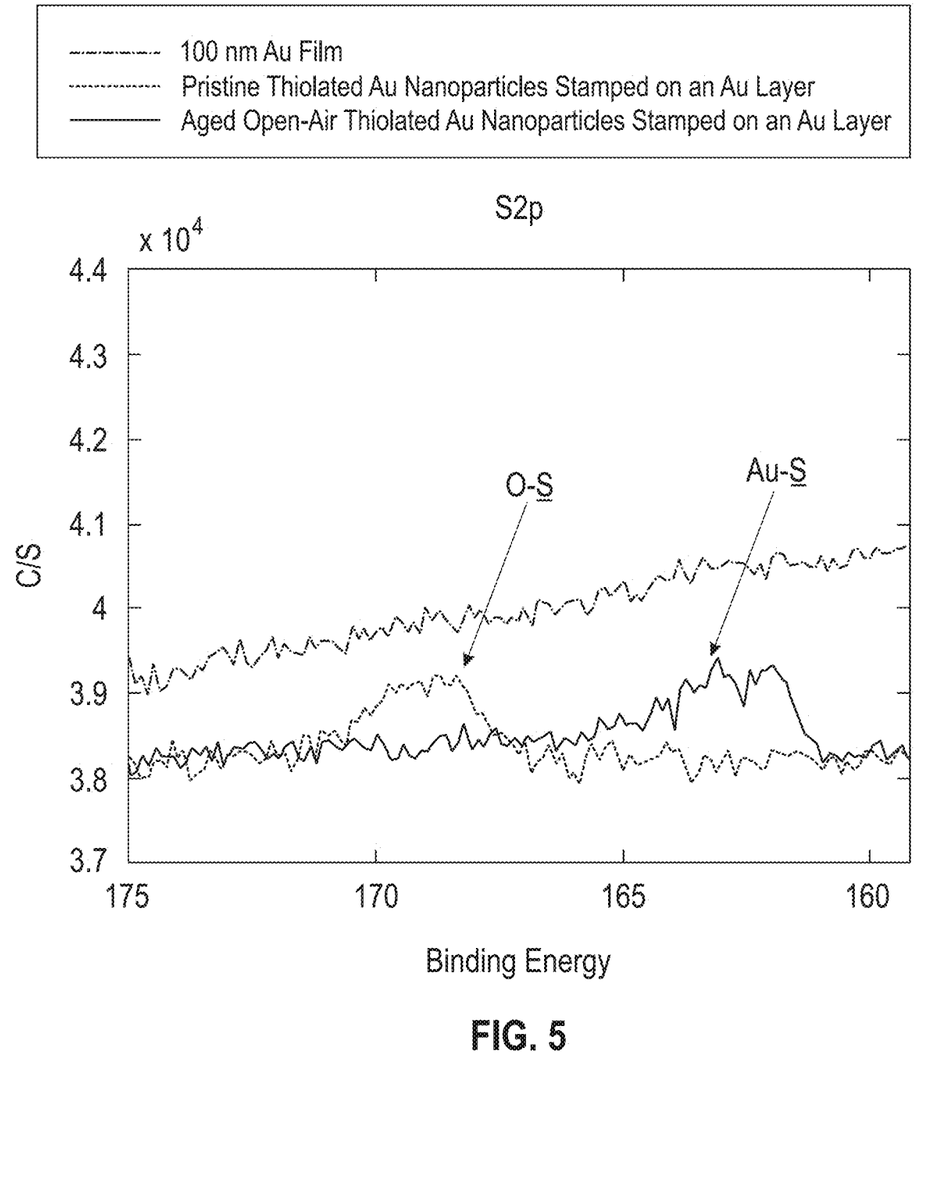
FIG. 5 is a graph showing XPS (x-ray photoelectron spectroscopy) spectra results for a pristine Au film, as well as decanethiol-ligated Au-NPs under pristine conditions and after 40-day aged ambient air conditions.

FIG. 5 shows XPS (x-ray photoelectron spectroscopy) spectra of the S2p and Si2s region of a layer of gold, pristine decanethiol-ligated Au-NPs stamped on a gold surface, and 40-day aged open-air decanethiol-ligated Au-NPs stamped on a gold surface. Comparison of the pristine and aged peaks shows that after the decanethiol-ligated Au-NPs were aged in open ambient air, the Au—S peak of the pristine sample was replaced by an O—S peak, confirming the degradation of the decanethiol-ligated Au-NPs in an open ambient air environment.

FIGS. 6A and 6B show SEM (scanning electron microscopy) micrographs of hexanethiol-ligated Au-NPs in a pristine state immediately after deposition (FIG. 6A) and aged in open ambient air for 13 days (FIG. 6B). The aggregation of the individual nanoparticles confirms that Au-NPs lose their protective ligand shells and agglomerate after exposure to freely exchanging ambient air.

FIG. 7 shows the relative change in current (Response) over time of sealed and aged decanethiol-ligated Au-NPs subjected for 400 seconds (t=100 sec to t=500 sec) to 12678 ppm of octane in an $N_2$ flow. Prior to exposure to the $N_2$ flow, the Au-NPs were stamped on interdigitated electrodes and stored in 25 mL of sealed ambient air for 14 days. While highly conductive pristine Au-NPs lose their ability to sense after exposure to open ambient air (not shown), sealed Au-NPs retain their ability to sense over prolonged periods of time, as is shown by the distinct response of the Au-NPs to the introduction and withdrawal of the 12678 ppm of octane between t=100 and t=500 in FIG. 7.

The results of Example 1 and FIGS. 4-7 demonstrate that storing sensors within an enclosed volume can extend the lifetime of the sensor. Example 2 and FIGS. 8 and 9 address the effect that potential gaseous species within the headspace of the enclosed volume may have on a sensor and methods to eliminate deleterious gases from the enclosure that may lead to degradation of the sensor from within.

FIG. 8 shows SERS spectra of decanethiol-ligated Au-NPs in a pristine condition immediately following deposition, after 24 hours of storage in an open-air environment, and after 24 hours of flushing with "zero-air" (a mixture of 80% nitrogen and 20% oxygen with no other species). The zero-air sample, like the pristine sample, had no peaks attributable to degradation of the ligands. By contrast, the open-air sample displayed a degraded spectrum similar to the 5 and 7-day aged open-air samples of FIGS. 4A and 4B, respectively. The results of FIG. 8 lead to the conclusion that open ambient air has one or more species that leads to ligand degradation and that such one or more species are not present in zero-air.

FIG. 9A is a schematic depicting the set-up used in Example 2 to introduce ozone contaminant into zero-air atmosphere and the transfer of the ozone-enriched zero-air to an Au-NP sensor. FIG. 9B shows SERS spectra of decanethiol-ligated Au-NPs after 24 hours of flushing with zero-air and after exposure to one hour of ozone enriched zero-air. The spectra of the ozone-enriched decanethiol-ligated Au-NPs is similar to the spectra of the decanethiol-ligated Au-NPs that were exposed to 24 hours of open-air in FIG. 8. The results of FIG. 9B confirm the deleterious effect of ozone on chemiresistive ligated gas sensors. In one application, a gas sensor enclosure may include one or more active carbon filter to remove ozone contaminants.

The gas enclosure described herein allow for the effective implementation of gas sensors that would normally suffer from a decrease in sensitivity or working life due to degradation resulting from exposure to contaminants. Due to simplicity of design, the enclosed gas sensing device does not require vacuum pumps or impractical power supplies and can be manufactured as a small, lightweight, and low-power portable device. The gas sensor enclosures have application for many industries, including, without limitation, incorporation into electronic nose and IoT devices that require accurate gas sensor that will provide accurate gas sensing results and will not degrade over time.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

Example 1

Confinement Effect on Chemiresistive Ligated Gold Nanoparticle Sensors

To test the extent of degradation of chemiresistive ligated Au-NPs, 30 nm Au-NPs were functionalized with decanethiol or hexanethiol ligands and aged from 4 to 12 days in freely exchanging open-air and separately in a sealed 25 mL vial under air. Decanethiol-ligated and hexanethiol-ligated Au-NPs were also freshly prepared as pristine controls. The pristine, open-air, and sealed ligated Au-NPs were stamped on top of a gold surface for material characterization via SERS, XPS, and SEM and on top of interdigitated gold electrodes for resistivity/gas sensing measurements.

Material Characterization Tests:

SERS was used to test the degradation of the ligands surrounding the Au-NPs. Open-air and sealed decanethiol-ligated Au-NPs aged for five days and open-air and sealed hexanethiol-ligated Au-NPs aged for seven days were used for the tests (all ligated Au-NPs were stamped on a gold surface). The SERS spectra results for the pristine, open-air, and sealed decanethiol-ligated Au-NPs are shown in FIG. 4A, and the SERS spectra results for the pristine, ambient, and sealed hexanethiol-ligated Au-NPs are shown in FIG. 4B. The SERS spectra results showed significant degradation of the open-air Au-NP samples, whereas the sealed Au-NP samples had SERS spectra profiles that were similar to the profiles for the pristine samples. The SERS profiles were similar for the decanethiol-ligated Au-NPs and the hexanethiol-ligated Au-NPs.

XPS was used to test the degree of degradation of the ligands surrounding the Au-NPs. Pristine and open-air decanethiol-ligated Au-NPs stamped on the gold surface were used for comparative testing with a 100 nm gold film used as a control. The open-air decanethiol-ligated Au-NPs were aged for 140+ days. The XPS results for the pristine and open-air Au-NP samples and the Au control are shown in FIG. 5. The presence of the O—S peak in the open-air Au-NP sample, rather than the Au—S peak seen in the pristine Au-NP sample, indicated that the protective decanethiol ligands surrounding the Au-NPs had degraded during the 40+ days of open ambient air storage.

SEM images were used to observe the effect that the degradation of the ligands has on the nanoparticles. Hexanethiol-ligated Au-NPs were imaged immediately after deposition on a gold surface and after aging for 13 days in open ambient air. As shown in FIGS. 6A and 6B, the aged Au-NP samples degraded and agglomerated as a result of the hexanethiol-ligated Au-NPs losing their protective ligand shells after exposure to open ambient air.

Resistivity Tests:

To test the charge transport resistant change that occurs during the degradation of ligated Au-NPs, the resistance of hexanethiol-ligated Au-NPs stamped on interdigitated gold electrodes was measured after storage for 4 days and 12 days in open ambient air and after the same amount of time in 25 mL sealed containers. The resistance of pristine samples was also measured. The results of the resistance change of the pristine, open-air, and sealed samples are shown in Table 1, along with the resistance ratio of the pristine samples to the aged samples.

TABLE 1

| Exposures Condition | Hexanethiol-ligated Au-NPs (Resistance Change in kΩ) | | | | |
|---|---|---|---|---|---|
| | Pristine | 4 days aged | 12 days aged | Ratio: Pristine/4 days | Ratio: Pristine/12 days |
| Ambient Air | 16000 kΩ | 350 kΩ | 0.12 kΩ | 46 | 133,333 |
| Sealed Air (25 mL) | 6200 kΩ | 2930 kΩ | 2170 kΩ | 2.1 | 2.9 |

The data in Table 1 show that the aggregation (i.e., ligand degradation) of hexanethiol-ligated Au-NPs is accompanied by drops in resistance from a pristine state to a 4-day old state (16000 kΩ to 350 kΩ) with a further drop in resistance from day 4 to day 12 (350 kΩ to 0.12 kΩ). The drop in the resistance from 16000 kΩ to 0.12 kΩ between the pristine state and the day 12 aging in open-air indicates that during the 12-day period, the Au-NP layers became highly conductive as a result of the degradation of the protective hexanethiol ligands surrounding the Au-NPs. By contrast, during the same 12-day period, the resistance of the Au-NP samples stored in the sealed containers changed from 6200 kΩ to 2170 kΩ, indicating a much lower extent of ligand degradation.

Decanethiol-ligated Au-NPs stamped on interdigitated electrodes and sealed in a 25 mL volume container for 14 days were also tested for degradation by introducing 12678 ppm of octane in an $N_2$ flow into the sealed container. The results of the degradation test are shown in FIG. 7, which plots current (Response) against time with the $N_2$ introduction occurring between t=100 sec and t=700 sec. The results in FIG. 7 show that the decanethiol-ligated Au-NPs reacted to both the influx and the removal of the gas confirming that the decanethiol-ligated Au-NPs had not degraded during the 14-day aging process within the sealed container.

Example 2

The Effect of Excluding Deleterious Compounds on Chemiresisitve Ligated Gold Nanoparticle Sensors To test for the presence of deleterious gases in a sensor environment, the following decanethiol-ligated Au-NPs stamped on top of a gold surface were tested via SERS: a pristine sample; an open-air sample aged for 24 hours; and a third sample exposed to a continuous stream of "zero-air" (i.e., a synthetic mixture containing 80% nitrogen, 20% oxygen, and no other species) for 24 hours. The SERS results shown in FIG. 8 confirm that the zero-air sample has a similar profile to the pristine sample indicating that the zero-air sample, like the pristine sample, had no ligand degradation. By contrast, the ambient air sample had a SERS spectrum indicating degradation of the protective decanethiol ligand by a substance in the open-air environment.

Since it is known that ozone can be responsible for Au—S bond degradation, ozone was added to the zero-air mixture by introducing an ozone generator between the zero-air source and the decanethiol-litigated Au-NP sample, the latter of which had remained under a continuous stream of zero-air for 24 hours. A schematic of the ozone zero-air set up is shown in FIG. 9A. The ozone generator was switched on and allowed to run for approximately 1 hour in order to form ozone in the zero-air stream by UV illumination (the gold surface substrate was not subjected to the UV light emitted by the ozone generator). A SERS spectrum of the ozone-exposed Au-NP sample was recorded and compared with the first 24-hour zero-air SERS spectrum that showed no ligand degradation. The SERS results shown in FIG. 9B confirmed that the introduction of the ozone into the zero-air stream resulted in a SERS spectrum that matched the open-air SERS spectrum of FIG. 8, both of which documented profiles indicating degradation of the ligands surrounding the Au-NPs.

We claim:

1. A method, comprising:
 (i) providing an enclosure comprising an inlet, at least one outlet, at least one retractable filter situated at the inlet, and a sensor that detects an analyte of interest;
 (ii) introducing a gas comprising the analyte of interest through the inlet, wherein the at least one retractable filter retracts so that the gas enters the enclosure as an unfiltered gas, the sensor detects the analyte of interest in the gas, the gas exits the enclosure through the at least one outlet after detection, the gas does not contact the at least one retractable filter between input of the gas through the inlet and exit of the gas through the at least one outlet, and the gas further includes at least one deleterious compound that degrades performance of the sensor;
 (iii) introducing an additional influx of the gas through the inlet, wherein the at least one retractable filter is repositioned so that the additional influx of the gas passes through the at least one retractable filter prior to contacting the sensor, wherein the at least one retractable filter removes the at least one deleterious compound from the additional influx of the gas; and
 (iv) allowing the additional influx of the gas that is free of the deleterious compounds to remain in contact with the sensor.

2. The method of claim 1, wherein the sensor is selected from the group consisting of a metal oxide thin film, a metal oxide nanostructure, and a metal nanoparticle.

3. The method of claim 2, wherein the sensor is a metal nanoparticle sensor, wherein the metal is selected from the group consisting of gold, silver, platinum, and palladium.

4. The method of claim 3, wherein the metal nanoparticle sensor is ligated with a thiol selected from the group consisting of ethanethiol, hexanethiol, octanethiol, decanethiol, dodecanethiol, and combinations thereof.

5. The method of claim 1, wherein the at least one retractable filter is selected from the group consisting of activated carbon, silica gel, and combinations thereof.

6. The method of claim 1, wherein the at least one retractable filter is a replaceable filter.

7. The method of claim 1, wherein the at least one deleterious compound is selected from the group consisting of ozone, silicone, chlorine, particulates, sediment, volatile organic compounds, and combinations thereof.

8. The method of claim 1, wherein the enclosure further comprises at least two valves, one of which opens and closes the inlet and another of which opens and closes at least one outlet.

9. The method of claim 8, wherein the inlet and one of the at least one outlet are open at step (ii) and both the inlet and the at least one outlet are closed at step (iv).

10. The method of claim 1, wherein the enclosure further comprises a sensing gas line, a purge gas line, and a valve at the inlet to direct the gas from the inlet into the sensing gas line and/or the purge gas line, wherein the sensing gas line has no filters and the at least one retractable filter is situated in the purging gas line.

11. The method of claim 1, wherein steps (ii) and (iii) operate in a time-frame ranging from one second to no longer than 12 hours.

12. A method, comprising:
 (i) providing an enclosure comprising an inlet, at least one outlet, at least one filter, and a sensor that detects an analyte of interest;
 (ii) introducing a gas comprising the analyte of interest through the inlet, wherein the sensor detects the analyte of interest in the gas, the gas exits the enclosure through the at least one outlet after detection, the gas does not contact the at least one filter between input of the gas through the inlet and exit of the gas through the at least one outlet, and the gas further includes at least one deleterious compound that degrades performance of the sensor;
 (iii) introducing an additional influx of the gas through the inlet, wherein the additional influx of the gas passes through the at least one filter prior to contacting the sensor, wherein the at least one filter removes the at least one deleterious compound from the additional influx of the gas; and (iv) allowing the additional influx of the gas that is free of the deleterious compounds to remain in contact with the sensor, wherein the enclosure further comprises a sensing gas line, a purge gas line, and a valve at the inlet to direct the gas from the inlet into the sensing gas line and/or the purge gas line, wherein the sensing gas line has no filters and the at least one filter is situated in the purging gas line.

13. The method of claim 12, wherein the sensor is selected from the group consisting of a metal oxide thin film, a metal oxide nanostructure, and a metal nanoparticle.

14. The method of claim 13, wherein the sensor is a metal nanoparticle sensor, wherein the metal is selected from the group consisting of gold, silver, platinum, and palladium.

15. The method of claim 14, wherein the metal nanoparticle sensor is ligated with a thiol selected from the group consisting of ethanethiol, hexanethiol, octanethiol, decanethiol, dodecanethiol, and combinations thereof.

16. The method of claim 12, wherein the at least one filter is selected from the group consisting of activated carbon, silica gel, and combinations thereof.

17. The method of claim 12, wherein the at least one filter is a replaceable filter.

18. The method of claim 12, wherein the at least one deleterious compound is selected from the group consisting of ozone, silicone, chlorine, particulates, sediment, volatile organic compounds, and combinations thereof.

19. The method of claim 12, wherein the enclosure further comprises at least two valves, one of which opens and closes the inlet and another of which opens and closes at least one outlet.

20. The method of claim 19, wherein the inlet and one of the at least one outlet are open at step (ii) and both the inlet and the at least one outlet are closed at step (iv).

21. The method of claim 12, wherein steps (ii) and (iii) operate in a time-frame ranging from one second to no longer than 12 hours.

* * * * *